US005781305A

United States Patent [19]
Downes

[11] Patent Number: 5,781,305
[45] Date of Patent: Jul. 14, 1998

[54] FIBER OPTIC TRANSMISSOMETER

[76] Inventor: Philip Downes, 15525 Grinnell Ter., Rockville, Md. 20855

[21] Appl. No.: 839,364

[22] Filed: Apr. 18, 1997

Related U.S. Application Data

[63] Continuation-in-part of Ser. No. 595,161, Feb. 1, 1996.
[51] Int. Cl.$^6$ .................................................. G01N 21/59
[52] U.S. Cl. ........................... 356/435; 356/436; 356/442; 250/575
[58] Field of Search .................................. 356/432, 433, 356/435, 436, 441, 442; 250/575

[56] References Cited

U.S. PATENT DOCUMENTS

| | | | |
|---|---|---|---|
| 3,146,293 | 8/1964 | Lesage | 356/435 |
| 3,976,369 | 8/1976 | McCardell et al. | 356/441 |
| 3,976,891 | 8/1976 | Parkinson | 250/575 |
| 4,037,973 | 7/1977 | Carr | 356/441 |
| 4,257,708 | 3/1981 | Fukuda | 356/435 |
| 4,416,542 | 11/1983 | Mooradian | 356/435 |
| 4,688,943 | 8/1987 | Modarress | 356/436 |

FOREIGN PATENT DOCUMENTS 277740  11/1989  Japan ....................... 356/442

*Primary Examiner*—Richard A. Rosenberger
*Attorney, Agent, or Firm*—Walter G. Sutcliff

[57] ABSTRACT

A transmissometer for measuring a volume attenuation coefficient of a column of water, including a transmissometer housing; a light source, producing an optical light beam; a Y-splitter, splitting the optical light beam into two light beams within the transmissometer housing; a pressure proof connector and two optical fibers, routing the two light beams outside the transmissometer housing; two collimators for collimating outputs of the two optical fibers prior to transmission through the column of water; a reflecting prism, reflecting the outputs of the two collimators back into the transmissometer housing via a sensor view port where a distance between a first of the two collimators and the reflecting prism is R1 and a distance between a second of the two collimators and the reflecting prism is R2; two detectors for detecting intensities I1 and I2 of the two light beams reflected by the reflecting prism; and a processor for determining the volume attenuation coefficient of the column of water according to:

$$\alpha = \Delta R^{-1} \ln(I_2/I_1)$$

where $\alpha$=volume attenuation coefficient of the column of water;
$\Delta R$=In water path length difference (R1−R2);
$I_1$=Intensity at the first of the two detectors; and
$I_2$=Intensity at the second of the two detectors.

62 Claims, 2 Drawing Sheets

——— PROPAGATION IN FIBER

– – – – – – FREE SPACE PROPAGATION

OPEN TO WATER

── PROPAGATION IN AIR
---- PROPAGATION IN WATER

── PROPAGATION IN FIBER
---- FREE SPACE PROPAGATION

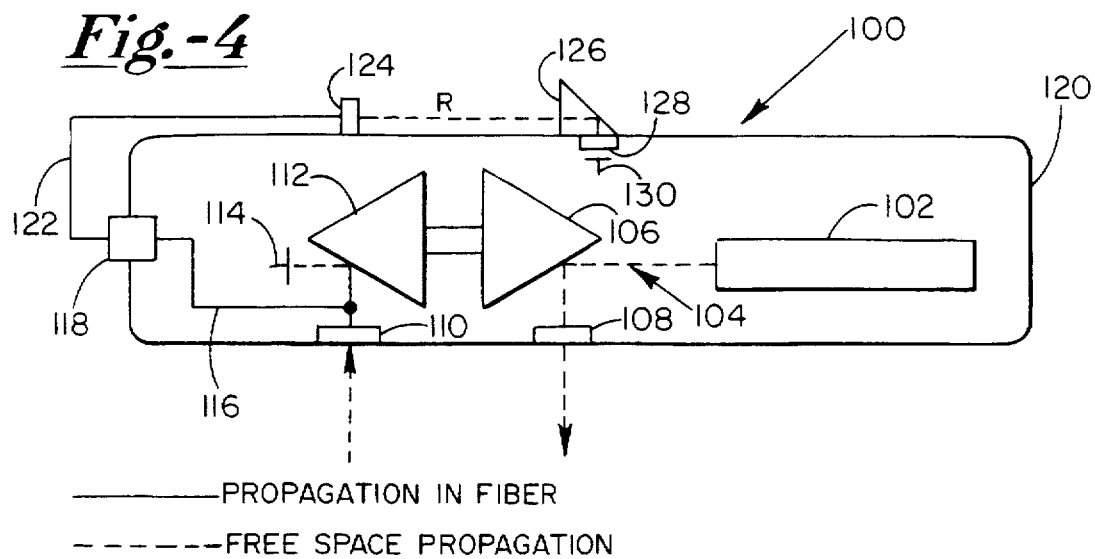

FIBER OPTIC TRANSMISSOMETER

This application is a continuation-in-part of application Ser. No. 08/595,161 filed on Feb. 1, 1996, the entire contents of which are hereby incorporated by reference.

BACKGROUND OF THE INVENTION

1. Field of the Invention

The present invention is directed to an underwater multipath transmissometer that eliminates transmission measurement errors associated with window fouling. A transmissometer is an instrument used to determine one of the inherent optical properties of a body of water, specifically the volume attenuation coefficient $\alpha$. The volume attenuation coefficient is one parameter used in the development of underwater imaging mission profiles. This parameter is used to predict the maximum permissible sensor-to-target distance that provides acceptable imagery through the water environment.

The present invention is also directed to a fiber optic-based transmissometer that can be used in conjunction with an underwater laser line scan imaging system to simultaneously measure the inherent water transmission quality during underwater imaging. This invention provides the capability to directly measure the transmission quality of the water environment which can then be used to determine the permissible sensor-to-target range for capturing high quality underwater imagery. This form of transmissometer can also form the basis of a closed feedback control loop which can be used for autonomous vehicle control. This invention eliminates the need for a separate optical transmissometer sensor reducing the cost, weight, size and power consumption of the underwater vehicle carrying the sensor suite. For autonomous vehicles, the savings in weight, volume and power will directly provide an extension of the vehicle's battery duration allowing mission time extension.

This multipath transmissometer provides a novel method and apparatus for measuring the volume attenuation coefficient of a body of water without the inaccuracies introduced by sensor window fouling. One application of transmissometer measurements is to predict allowable sensor-to-target range used in underwater imaging applications. The fouling-induced measurement error can severely impact the predictions leading to large uncertainties in underwater imaging mission planning.

A fiber optic transmissometer also provides a method and apparatus for simultaneously measuring water quality during image capture by a laser line scan underwater imaging system. Knowledge of the water quality, which directly impacts the image quality captured by an underwater optical sensor, can be used to make sensor-to-target predictions necessary for capturing high quality image data. Operating at the longest acceptable sensor-to-target distance allows maximum swath width coverage, thereby minimizing mission duration or extending survey area coverage. Pre-survey water quality measurements can also be eliminated, thereby minimizing deployment costs. This invention will result in lower costs for underwater optical collection missions and reduce the size, weight and power consumption of underwater vehicles.

2. Description of the Prior Art

A conventional transmissometer 10, as illustrated in FIG. 1, is housed in a pressure vessel 12 and includes a light source 14 (typically an incandescent or Xenon flash), an optical bandpass filter (not shown), a plurality of optical windows 16, two water propagation portions 18, supported by a support structure 20, an air propagation portion 22, a reflecting prism assembly 24, and a detector 26. The conventional transmissometer 10 measures a broadband transmission coefficient typically on the order of 20–50 nm wide, centered within the water's visible light transmission window. This conventional transmissometer 10 is prone to window fouling of the plurality of optical windows 16, during deployment, either by surface oil or particulate matter, which attenuate the light independent of the water volume. Window fouling introduces a measurement error indicating a water volume attenuation coefficient that is higher than the actual value of the water volume. This in turn decreases the prediction of maximum sensor-to-target range for underwater imaging sensors leading to increased mission duration or loss of coverage for fixed energy systems.

As stated above, the conventional transmissometer 10 illustrated in FIG. 1 measures a broadband transmission coefficient (equal to $1/\alpha$, where $\alpha$ is the volume attenuation coefficient) typically on the order of 20–50 nm wide, centered within the water's visible light transmission window. Since the light source 14 is not monochromatic, the broadband measurement does not provide accurate transmission quality measurements for making sensor-to-target imaging predictions when used in conjunction with a monochromatic imaging system such as a laser line scanner. Further, existing transmissometers are expensive, heavy and require a large volume allocation on systems where space and power are limiting design factors.

SUMMARY OF THE INVENTION

This invention provides a novel method and apparatus for measuring the volume attenuation coefficient of a body of water without introducing a measurement error associated with window fouling. Transmissometers are typically used to determine the volume attenuation coefficient of water which is required to predict allowable sensor-to-target ranges for underwater imaging. A transmissometer which is not subject to window fouling will allow for more accurate predictions of maximum sensor-to-target ranges, thereby increasing the effectiveness of underwater imaging missions.

This invention also provides a method and apparatus for measuring the transmission characteristics of the water while simultaneously imaging through the water volume. The method and apparatus of the present application result in significant cost savings by eliminating the need for pre-survey water quality measurements and eliminating the need for an additional large, heavy and expensive transmissometer system.

These and other objects of the present invention will become more readily apparent from the detailed description given hereafter. However, it should be understood that detailed description of the specific examples, while indicating preferred embodiments in the invention are given by way of illustration only, since various changes and modification within the spirit and scope of the invention will become apparent to those skilled in the art from the detailed description.

BRIEF DESCRIPTION OF DRAWINGS

The following detailed description of the invention will be more readily understood when considered in conjunction with the accompanying drawings:

FIG. 4 illustrates an underwater laser line scanning system in another embodiment of the present invention; and FIG. 5 illustrates the geometry of a laser line scan underwater imaging system, using the transmissometer of the present invention.

Further scope of applicability of the present invention will become apparent from the detailed description given hereafter. However, it should be understood that the detailed description and specific examples, while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1:
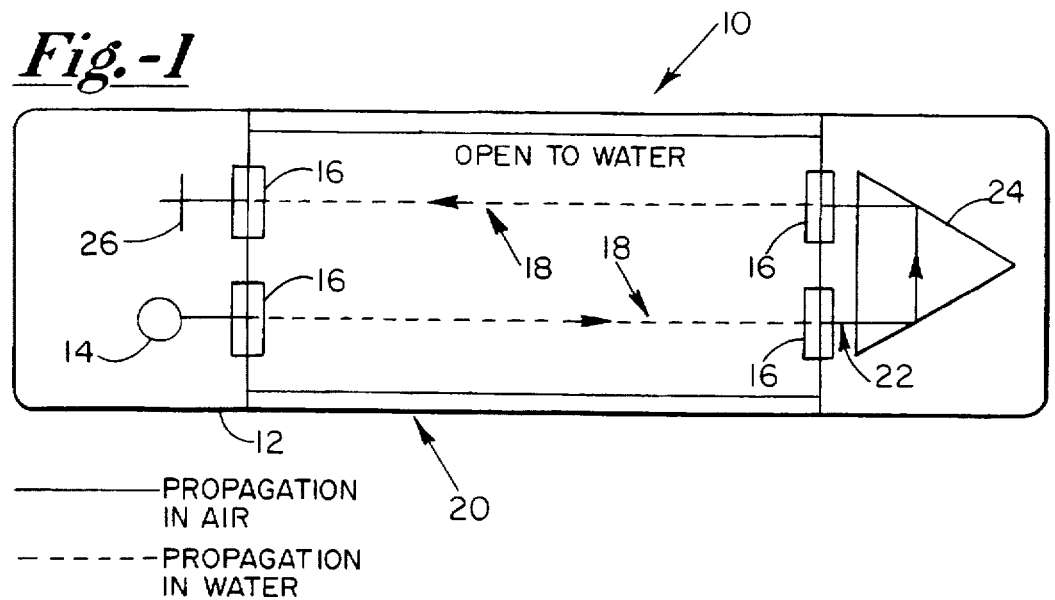
FIG. 1 illustrates a conventional transmissometer.
Figure 2:
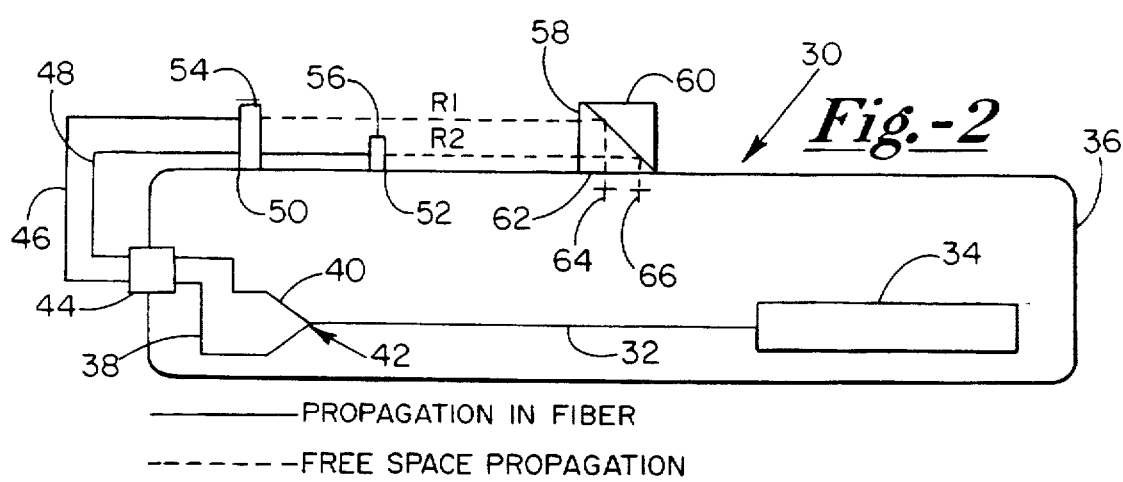
FIG. 2 illustrates a transmissometer in one embodiment of the present invention.

This invention is directed to a novel transmissometer, illustrated in FIG. 2, that prevents the errors associated with optical window fouling, discussed above with respect to conventional transmissometers. The novel transmissometer of the present invention includes the following novel features:

(1) splitting the light source output into two distinct collimated optical beams;

(2) mechanically shortening the throughwater path length of one beam to provide a path difference through the water volume; and (3) adding a second linear detector to measure the intensity of the two beams independently.

The outputs from the two detectors are then used to calculate the volume attenuation coefficient α of the water volume from the following equation:

$$\alpha = \Delta R^{-1} \ln(I_2/I_1) \quad (1)$$

where

α=Volume attenuation coefficient;

ΔR=In water path length difference (R1–R2);

R1=In-water path length for beam 1;

R2=In-water path length for beam 2;

$I_1$=Intensity at detector D1; and $I_2$=Intensity at detector D2.

As illustrated in FIG. 2, the transmissometer 30 of the present invention includes an optical fiber 32 which is coupled to a light source 34, which may be a laser light source, located inside a pressure vessel 36. Light traveling through the optical fiber 32 is separated into two different fibers 38 and 40 using a 50/50 Y-splitter 42. The two fibers 38 and 40 are then passed through a pressure-proof connector 44 and routed outside of the pressure vessel 36, where two protected fibers 46 and 48 are mechanically attached to an exterior surface of the pressure vessel 36 using holding fixtures 50 and 52. Collimating optics 54 and 56, held by holding fixtures 50 and 52, are located at the end of the two protected fibers 46 and 48 to collimate diverging light outputs of the two protected fibers 46 and 48. Collimation can be realized by fusion splicing a cutback length of gradient index (GRIN) fiber onto the end of the two protected fibers 46 and 48. A collimated beam is then projected from collimating optics 54 and 56 onto a reflecting prism 58, in a housing 60, attached to the pressure vessel 36, which reflects the incident light through a sensor view port 62 onto two detector modules 64 and 66. The detector modules 64 and 66 are connected to a data processor and/or recorder 70 which may be components of the transmissometer 30 or components of an overall underwater laser line scanning system of which transmissometer 30 is also a component.

The transmissometer 30 of the present invention operates as follows. The light source 34 emits light which is coupled into the optical fiber 32. An output of the optical fiber 32 is split by 50-50 Y-splitter 42 and propagated through two different fibers 38 and 40. The two different fibers 38 and 40 are connected to connector 44 and coupled to two protected fibers 46 and 48, which are located outside the pressure vessel 36. Outputs of the two protected fibers 46 and 48 are optically coupled with collimating optics 54 and 56. Outputs of the collimating optics 54 and 56 are directed toward the reflecting prism 58. The distance between the collimating optics 54 and the reflecting prism 58 is R1 and the distance between the collimating optics 56 and the reflecting prism is R2. Output light from the collimating optics 54 and 56 is reflected by the reflecting prism 58, through the sensor viewport 62, and impinged on detector 64 and 66. Detector modules 64 and 66, detect the intensity of light output from collimating optics 54 and 56, respectively. The detector modules 64 and 66 convert optical input signals to analog electrical signals whose output amplitude is proportional to the incident optical power. The detector modules 64 and 68 also convert the analog electrical signals to digital signals using an A/D converter. The digital signals are transferred to an internal data processor/recorder 70 over data interface cable 68 or an external data processor/recorder 70' via data interface cable 68' that passes through water tight bulk head connector 72. In one preferred embodiment, the internal data processor/recorder 70 is contained within the transmissometer housing 36. In another preferred embodiment the external data processor/recorder 70' is not contained within the transmissometer housing 36. The volume attenuation coefficient α, of the water volume located betwen the collimating optics 54 and 56 and the reflecting prism 58 is defined by Equation (1). The volume attenuation coefficient α of the water volume is utilized to determine maximum sensor-to-target imaging predictions.

In the preferred embodiment, the protected fibers 46 and 48 have core diameters of approximately 140 microns. Further, the difference between R1 and R2 is greater than or equal to ½ meter.

In another preferred embodiment, the light source 34 is a frequency doubled Nd/YAG (neodymium yttrium aluminum garnet) solid state laser light source. In another preferred embodiment, the light source 34 is an argon ion gas laser. In another preferred embodiment, the light source 34 is a zenon flash, which is a flash tube filled with zenon gas and electrically exited. In another preferred embodiment, the light source 34 is an incandescent lamp.

In another preferred embodiment, the optical fiber 32 has a large core diameter, with a high numeric aperture. A higher numeric aperture permits the coupling of more power and provides a better signal-to-noise ratio. Further, a higher numeric aperture also permits easier fabrication and alignment of the optical elements. In a preferred embodiment, the numeric aperture is greater than 0.29.

In another preferred embodiment, the optical fiber 32 is a standard commercial multimode fiber.

In another preferred embodiment, the 50/50 Y-splitter 42 is a standard one-by-two splitter. In another preferred embodiment, the 50/50 Y-splitter 42 is a wave guide splitter or a fused splitter. However, a wave guide splitter is preferred over the fused splitter, since the wave guide splitter is more thermally stable. In a fused splitter, the output in each leg varies as a function of temperature. In a preferred embodiment, the 50/50 Y-splitter 42 is a Corning Wave Guide Splitter.

In addition, in another preferred embodiment, the 50/50 Y-splitter 42 could be a 33/67 splitter. Such a splitter generates a more statistically significant signal-to-noise ratio, but requires more data processing.

In the preferred embodiment, the connector 44 is compatible with the type of fiber chosen for optical fiber 32.

In another preferred embodiment, the two protected fibers 46 and 48 are waterproof and hermetically sealed.

In another preferred embodiment, collimating optics 54 and 56 are gradient index (GRIN) lenses, whose size is dependent on the numeric aperture of the optical fiber 32. In a preferred embodiment, the collimating optics 54 and 56 are approximately 1–2 millimeters in diameter. Further, the GRIN lenses themselves, act as the optical windows.

In another preferred embodiment, collimating optics 54 and 56 are microlenses.

In another preferred embodiment, the housing 60 is a prism holding fixture, which holds the reflecting prism 58 to the pressure vessel 36.

In another preferred embodiment, the sensor viewport 62 is a is a quartz or sapphire window, which is compatible with the wavelength of the light emitted from the light source 34 and the depth of the water at which the transmissometer 30 is being utilized.

In another preferred embodiment, detector modules 64 and 66 include silicon detectors, having low noise and high responsivity to the transmitted wavelength of the light source 34.

The transmissometer 30, illustrated in FIG. 2, is calibrated in air, in order to change the DC gain and bias of the detector modules 64 and 66, such that their outputs match. Due to the different lengths of R1 and R2, this calibration cannot be performed in water.

The transmissometer disclosed in the present invention provides an accurate measurement of the volume attenuation coefficient α. Further, the transmissometer of the present invention may be used in an autonomous vehicle, such as an unmanned submersible vehicle for making accurate maximum sensor-to-target predictions to obtain high quality optical imagery or for performing water quality research.

Using a collimated beam approach allows the unit to be calibrated in air prior to deployment. The purpose of this calibration is to eliminate any DC gain and bias offset due to detector responsivity variations or differences in the light source output from each of the two protected fibers 46 and 48.

Figure 3A:
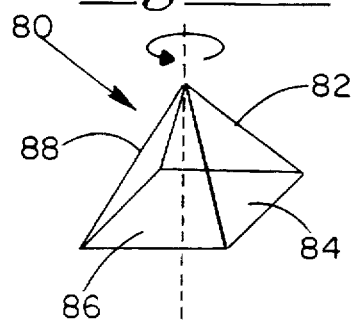
FIG. 3(a) illustrates a scan mirror in another embodiment of the present invention.
Figure 3B:
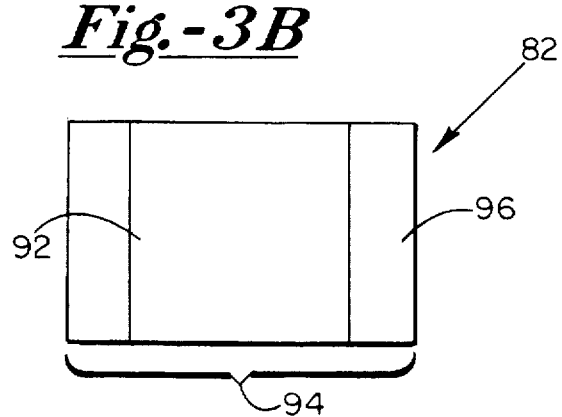
FIG. 3(b) illustrates a mirror facet of the scan mirror of FIG. 3(a)

In another embodiment, the present invention is directed to a transmissometer which uses a portion of output light from an underwater laser line scan imaging system to measure the transmission quality of the water environment. The underwater laser line scan imaging system creates an image by projecting a laser beam into the water column and then senses the return signal with an optical detector that is synchronously scanned with the laser spot. In this way, the underwater laser line scan imaging system creates a reflectance map of the sea floor bottom and targets which are subsequently displayed on a CRT. Synchronous scanning is produced by two pyridimal scan mirrors, a projector mirror and a scanning mirror, which are driven to rotate by a common drive motor: one for directing the laser beam across the bottom and one for scanning the detector. As illustrated in FIG. 3(a), scan mirror 80 is divided into 90° facets 82, 84, 86, and 88 each of which produces a new line of data. Due to edge effects, only a 70° field 92 of the total 90° output field 94 of view is actually used for projecting image forming light into the water column, as illustrated in FIG. 3(b). In the present invention, a portion of light from the unused 20° field 96 of the scan mirror is captured by an optical pick off fiber and utilized for the transmission measurement.

The optical pick off fiber is routed outside of a pressure vessel through a watertight connector. The pick off fiber is attached to the outside of the pressure vessel using a holding fixture. Collimating optics are located at the output of the fiber to collimate the light prior to transmission through the water path. One simple method for collimating the output from the fiber is to fusion splice a length of gradient index (GRIN) fiber onto the end of the transmission fiber. The collimated light is then projected toward a reflecting prism where it is redirected into a detector module located behind a pressure resistant window.

In more detail, as illustrated in FIG. 4, the underwater laser line scanning system 100 in the second embodiment of the preferred invention, includes a light source 102, such as a laser light source, which emits an optical beam 104. The optical beam is reflected by scanning mirror 106 and either output through output window 108 outside of the underwater laser line scanner 100 or output into an end of the optical pick off fiber 116. By proper positioning of the output window 108 and the end of the optical pick off fiber 116, and by correct rotation of the projecting mirror 106, the light reflected by the 70° portion 92 of the facet 82 is projected through the output window 108 and into the water column and the light reflected by the 20° portion 96 of the facet 82 is projected into the end of the optical pick off fiber 116. The optical beam projected through the water column reenters the underwater laser line scanner 100 via an input window 110 and is reflected by a projection mirror 112 to a detector 114. The detector 114 is utilized to produce the output of the underwater laser line scan imaging system, using another processor/recorder (not shown).

The pick off fiber 116 is located between the output window 108 and the projection mirror 106. It is the pick off fiber 116 which provides the light necessary for determining the volume attenuation coefficient a of the water volume. The pick off fiber 116 is fed to connector 118 outside the pressure vessel 120. A protected fiber 122 is connected to the connector 118 and spliced to collimating optics 124. An output of the collimating optics 124 travels a distance R in free space, and is reflected by reflecting prism 126. The light reflected by the reflecting prism 126 passes through input window 128 and impinges upon detector module 130. The detector module 130 converts the optical input signal to an analog electrical signal whose output amplitude is proportional to the incident optical power. Further, the detector module 130 converts the analog electrical signal to a digital signal using an A/D converter. The digital signal is transferred to an internal/external data processor and/or recorder 132, 132' over an existing laser line scanner data interface cable 134, 134'.

The volume attenuation coefficient α of the water volume is then determined as follows. Prior to deployment, a detector calibration constant is obtained by measuring the beam attenuation in air. The first portion of this calibration includes blocking the input window 126 such that no light reaches the detector 130. A DC offset level is determined to zero adjust the detector 130 output readings. The underwater laser line scanning system 100 is then operated in air. Since the beam has been collimated, there will be a four percent Fresnel reflectance loss at each air/water interface. The measured intensity in air will therefore reflect a transmission coefficient of 92 percent. A gain factor is calculated to account for the Fresnel loss which will not occur once the underwater laser line scanning system 100 is placed in water. After calibration, the underwater laser line scanning system 100 is deployed. At periodic intervals, the detector 130 output is sampled to determine the beam transmission through the water path. Using this data, the following equations are used to determine the water transmission characteristics.

The relationship betwen the measured intensity and the water transmission quality can then be found using the well known equation:

$$I = I_o e^{-\alpha R}$$

where,

I=Measured intensity after transmission through the water path at the detector 130 (changes as a function of water quality)

$I_o$=Calibrated intensity of the transmitted light in air |constant|

α=Volume attenuation coefficient |1/meter|

R=The path length through the water volume |meters|

Solving for the unknown volume attenuation coefficient yields the relationship.

$$\begin{aligned}\alpha &= -1/R \ln(I/I_o) \\ &= R^{-1} \ln(I_o/I) \\ &= R^{-1} \ln(1/T)\end{aligned} \quad (2)$$

where T is the transmittance of the water volume and equals $$\frac{I}{I_o}$$

The underwater laser line scanning system 100 of the present invention operates as follows. The light source 102 emits an optical beam 104, which is reflected by scanning mirror 106.

An optical pick off fiber 116 is located between the output window 108 and the projection mirror 106. The optical pick off fiber 116 is fed to a connector 118 on an exterior of the pressure vessel 120. The connector 118 is connected to protected fiber 122, which is terminated at collimating optics 124. An output of the collimating optics 124 is directed toward the reflecting prism 126. The distance between the collimating optics 124 and the reflecting prism 126 is R. Output light from the collimating optics 124 is reflected by reflecting prism 126, through input window 128 and impinged on detector module 130. Detector module 130 detects the intensity of light output from collimating optics 124. The volume attenuation coefficient α of the water volume located between the collimating optics 124 and the reflecting prism 126 is defined by Equation 2. The volume attenuation coefficient α is then used to determine maximum sensor-to-target imaging predictions.

In another preferred embodiment, the multipath transmissometer is used in conjunction with the laser line scan system benefitting from the more accurate volume attenuation coefficient determination while reducing the size, weight and power of the overall system.

The intensity of light emitted from the output window 108, the sensitivity of the detector 130, the volume attenuation coefficient α, the reflectance of the target in the water column, and the required probability of detecting the target in the water column are all a function of the wavelength of the light emitted through the output window 108 and also define a permissible sensor-to-target range. FIG. 5 illustrates that the accurate determination of the volume attenuation coefficient α permits maximum sensor-to-target range to be determined.

In FIG. 5, an underwater laser line scanning system 140 is located a distance $H_1$ from the target, which in this case is the ocean bottom 142. With an incorrect volume attenuation coefficient α, which include a factor associated with window fouling, the diameter of the area capable of being imaged by the underwater laser line scanning system 140 is $D_1$. However, if the actual volume attenuation coefficient α corrected for window fouling is utilized, as set forth in the method and apparatus of the present invention, the underwater laser line scanning system 140 may be located a distance $H_2$ from the target of interest, namely the ocean bottom 142. As a result, a larger area, having a diameter of $D_2$ may be imaged. As a result, the coverage for the fixed energy system utilizing the transmissometer of the present invention is increased and the required image quality is maintained.

The present invention, in its various embodiments, has applications in autonomous vehicle control, as well as basic research on inherent water quality parameters. Further, the present invention, in its various embodiments, is suitable for offshore commercial inspection and survey applications. The multipath transmissometer, in its various embodiments, is unique in that it utilizes a multipath technique, namely paths R1 and R2 which provides two distinct path lengths through the water volume, which eliminates measurement errors due to window fouling. Additionally, the present invention in its various embodiments, utilizes fiber optics to route optical signals, which reduces the complexity and adds flexibility to the transmissometer of the present invention. The present invention, in its various embodiments, is also unique in that it uses a laser source to provide the optical signals, which enhances the reliability of the transmissometer of the present invention and allows narrow band measurements to be made.

The present invention also utilizes fiber optic transmissions to transmit light from the source through the water volume, which makes the present invention flexible, easy to implement, and permits the path length to be easily adjusted to obtain a more accurate volume attention coefficient measurement. Finally, the present invention can utilize coincident measurements for both the imaging system and the volume attenuation coefficient, utilizing the same imaging system light source. This permits the present invention to more directly measure inherent water characteristics at the same wavelength as the imaging light source and allows a simultaneous measurement of the water quality while imaging is being performed, using the imaging sensor light source.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A transmissometer for measuring a volume attenuation coefficient of a column of water, comprising:

a transmissometer housing;

light source means for producing light, splitting the light into two beams within said transmissometer housing.

and routing the two beams in two optical fibers, outside said transmissometer housing;

two collimators, collimating two outputs of the two optical fibers prior to transmission through the column of water;

a reflecting prism, reflecting the two outputs of said two collimators back into said transmissometer housing via a sensor view port, wherein a distance between a first of said two collimators and said reflecting prism is R1 and a distance between a second of said two collimators and said reflecting prism is R2;

two detectors, detecting intensities I1 and I2 of 19 the two outputs reflected by said reflecting prism; and processing means for determining the volume attenuation coefficient of the column of water according to:

$$\alpha = \Delta R^{-1} \ln(I_2/I_1)$$

where $\alpha$=volume attenuation coefficient of the column of water;
$\Delta R$=In water path length difference (R1–R2);
$I_1$=Intensity at the first of said two detectors; and
$I_2$=Intensity at the second of said two detectors.

2. The transmissometer of claim 1, wherein said transmissometer is a component of an underwater laser line scanning system.

3. The transmissometer of claim 2, wherein the volume attenuation coefficient determined by said processing means permits said underwater laser line scanning system to operate at a longest acceptable sensor-to-target distance.

4. The transmissometer of claim 1, wherein said light source means includes a laser light source.

5. The transmissometer of claim 4, wherein said laser light source is one of a solid state laser source and an argon laser source.

6. The transmissometer of claim 1, wherein $\Delta R \geq \frac{1}{2}$ meter.

7. The transmissometer of claim 1, wherein said light source means splits the light into the two beams such that the two beams have a 1:1 intensity ratio.

8. The transmissometer of claim 1, wherein said two optical fibers are attached to an outside of said transmissometer housing with holding fixtures.

9. The transmissometer of claim 1, wherein said transmissometer removes an error associated with window fouling of said two collimators and said reflecting prism.

10. An underwater laser line scanning system comprising:
a transmissometer, including
a transmissometer housing,
light source means for producing light, splitting the light into two beams within said transmissometer housing, and routing the two beams in two optical fibers, outside said transmissometer housing,
two collimators, collimating two outputs of the two optical fibers prior to transmission through the column of water, and
a reflecting prism, reflecting the outputs of said two collimators back into said transmissometer housing via a sensor view port, wherein a distance between a first of said two collimators and said reflecting prism is R1 and a distance between a second of said two collimators and said reflecting prism is R2;
two detectors, detecting intensities I1 and I2 of the two outputs reflected by said two collimators; and
processing means for determining the volume attenuation coefficient of the column of water according to:

$$\alpha = \Delta R^{-1} \ln(I_2/I_1)$$

where $\alpha$=volume attenuation coefficient of the column of water;
$\Delta R$=In water path length difference (R1–R2);
$I_1$=Intensity at the first of said two detectors; and
$I_2$=Intensity at the second of said two detectors.

11. A method of measuring a volume attenuation coefficient of a column of water with a transmissometer, comprising the steps of:

a) producing light, splitting the light into two beams within a transmissometer housing, and routing the two beams in two optical fibers, outside the transmissometer housing;

b) collimating two outputs of the two optical fibers prior to transmission through the column of water;

c) reflecting the two outputs of said step b) back into the transmissometer housing via a sensor view port;

d) detecting intensities I1 and I2 of the two outputs reflected in said step c); and e) determining the volume attenuation coefficient of the column of water according to:

$$\alpha = \Delta R^{-1} \ln(I_2/I_1)$$

where $\alpha$=volume attenuation coefficient of the column of water;
$\Delta R$=In water path length difference (R1–R2);
R1=In-water path length for a first of the two outputs of said step b);
R2=In-water path length for a second of the two outputs of said step b);
$I_1$=Intensity of the first of the two outputs of said step b); and
$I_2$=Intensity of the second of the two outputs of said step b).

12. The method of claim 11, the light produced in said step a) is produced by a laser light source.

13. The method of claim 12, wherein the laser light source is one of a solid state laser source and an argon laser source.

14. The method of claim 11, wherein $\Delta R \geq \frac{1}{2}$ meter.

15. The method of claim 11, wherein said step a), the light is split into the two beams such that the two beams have a 1:1 intensity ratio.

16. The method of claim 11, wherein the two optical fibers are attached to an outside of the transmissometer housing with holding fixtures.

17. The method of claim 11, wherein said method removes an error associated with window fouling of the transmissometer.

18. An underwater laser line scanning system comprising:
a housing;
propagating means for propagating light through a column of water onto a surface below the column of water;
receiving means for receiving light reflected by the surface below the column of water;
an optical pickoff fiber, diverting a portion of the light propagated by said propagating means, and routing said optical pickoff fiber inside said housing,
collimating means for collimating the portion of the light prior to transmission through the column of water, and
a reflecting prism, reflecting the portion of light collimated by said collimating means back into said transmissometer housing via a sensor view port, wherein a distance between said collimating means and said reflecting prism is R;

detector means for detecting an intensity I of the portion of the light reflected by said reflecting prism; and processing means for determining the volume attenuation coefficient of the column of water according to:

$$\alpha = R^{-1}\ln(1/T)$$

where $T=I/I_o$ and $I_o=$a calibrated intensity of the propagated light reflected in air.

19. The underwater laser line scanning system of claim 18, wherein said light source means includes a laser light source.

20. The underwater laser line scanning system of claim 19, wherein said laser light source is one of a solid state laser source and an argon laser source.

21. The underwater laser line scanning system of claim 18, wherein said processing means calculates the volume attenuation coefficient simultaneously with detection operations of said underwater laser line scanning system.

22. The underwater laser line scanning system of claim 18, wherein an output of said receiving means is utilized to produce a reflectance map of the surface below the column of water.

23. The underwater laser line scanning system of claim 18, said propagating means including a pyramidal scanning mirror and said receiving means including a pyramidal projecting mirror operating synchronously with said pyramidal scanning mirror to produce a reflectance map.

24. The underwater laser line scanning system of claim 23, said pyramidal scanning mirror including four sides of 90°, wherein a first portion of each of said four sides are used to propagate the light through the column of water and a second portion of each of said four sides provides the portion of the light to said optical pickoff fiber.

25. The underwater laser line scanning system of claim 24, wherein the first portion of each of said four sides is 70° and the second portion of each of said four sides is 20°.

26. A method of measuring a volume attenuation coefficient of a column of water with an underwater laser line scanning system comprising the steps of:

a) propagating light through a column of water onto a surface below the column of water;

b) receiving light reflected by the surface below the column of water;

c) diverting a portion of the light propagated in said step a) and routing the portion of the light inside of a housing of the underwater laser line scanning system;

d) collimating the portion of the light prior to transmission through the column of water;

e) reflecting the portion of light collimated in said step d) back into the housing for the underwater laser line scanning system via a sensor view port;

f) detecting an intensity I of the portion of the light reflected in said step e); and g) determining the volume attenuation coefficient of the column of water according to:

$$\alpha = R^{-1}\ln(1/T)$$

where
$T=I/I_o$,
R=in-water path length for the portion of light collimated in said step d) and
$I_o=$a calibrated intensity of the propagated light reflected in air.

27. The method of claim 26, wherein the portion of the light is diverted in said step c) with an optical pickoff fiber.

28. The method of claim 26, wherein the portion of the light is reflected in said step d) with a reflecting prism.

29. The method of claim 26, wherein said step g) determines the volume attenuation coefficient simultaneously with detection operations of said underwater laser line scanning system.

30. The method of claim 26, wherein an output of said step b) is utilized to produce a reflectance map of the surface below the column of water.

31. The method of claim 26, wherein the light is propagated in said step a) using a pyramidal scanning mirror and the light is received in said step b) using a pyramidal projecting mirror, operating synchronously with the pyramidal scanning mirror to produce a reflectance map.

32. The method of claim 31, wherein the pyramidal scanning mirror including four sides of 90° wherein a first portion of each of the four sides are used to propagate the light through the column of water and a second portion of each of the four sides provide the portion of the light diverted in said step c).

33. The method of claim 32, wherein the first portion of each of said four sides is 70° and the second portion of each of said four sides is 20°.

34. An underwater laser line scanning system comprising:

a housing;

propagating means for propagating light through a column of water onto a surface below the column of water;

receiving means for receiving light reflected by the surface below the column of water;

an optical pickoff fiber, diverting a portion of the light propagated by said propagating means, splitting the portion of the light into two beams within said housing and routing the two beams in two optical fibers, outside said housing;

two collimators, collimating two outputs of the two optical fibers prior to transmission through the column of water;

a reflecting prism, reflecting the two outputs of said two collimators back into said housing via a sensor view port, wherein a distance between a first of said two collimators and said reflecting prism is R1 and a distance between a second of said two collimators and said reflecting prism is R2;

two detectors for detecting intensities I1 and I2 of the two outputs reflected by said reflecting prism; and processing means for determining the volume attenuation coefficient of the column of water according to:

$$\alpha = \Delta R^{-1}\ln(I_2/I_1)$$

where
$\alpha=$volume attenuation coefficient of the column of water;
$\Delta R=$In water path length difference (R1−R2);
$I_1=$Intensity at the first of said two detectors; and
$I_2=$Intensity at the second of said two detectors.

35. The underwater laser line scanning system of claim 34, wherein said propagating means includes a laser light source.

36. The underwater laser line scanning system of claim 35, wherein said laser light source is one of a solid state laser source and an argon laser source.

37. The underwater laser line scanning system of claim 34, wherein $\Delta R \geq \frac{1}{2}$ meter.

38. The underwater laser line scanning system of claim 34, wherein said optical pickoff fiber splits the light into the two beams such that the two beams have a 1:1 intensity ratio.

39. The underwater laser line scanning system of claim 34, wherein said two optical fibers are attached to an outside of said housing with holding fixtures.

40. The underwater laser line scanning system of claim 34, wherein said underwater laser line scanning system removes an error associated with window fouling of said two collimators and said reflecting prism.

41. The underwater laser line scanning system of claim 34, wherein the volume attenuation coefficient determined by said processing means permits said underwater laser line scanning system to operate at a longest acceptable sensor-to-target distance.

42. The underwater laser line scanning system of claim 34, wherein said processing means determines the volume attenuation coefficient simultaneously with detection operations of said underwater laser line scanning system.

43. The underwater laser line scanning system of claim 34, wherein an output of said receiving means is utilized to produce a reflectance map of the surface below the column of water.

44. The underwater laser line scanning system of claim 34, said propagating means including a pyramidal scanning mirror and said receiving means including a pyramidal projecting mirror operating synchronously with said pyramidal scanning mirror to produce a reflectance map.

45. The underwater laser line scanning system of claim 44, said pyramidal scanning mirror including four sides of 90°, wherein a first portion of each of said four sides are used to propagate the light through the column of water and a second portion of each of said four sides provides the portion of the light to said optical pickoff fiber.

46. The underwater laser line scanning system of claim 45, wherein the first portion of each of said four sides is 70° and the second portion of each of said four sides is 20°.

47. A method of measuring a volume attenuation coefficient of a column of water with an underwater laser line scanning system comprising the steps of:
  a) propagating light through a column of water onto a surface below the column of water;
  b) receiving light reflected by the surface below the column of water;
  c) diverting a portion of the light propagated in said step a), splitting the portion of the light into two beams within a housing of the underwater laser line scanning system and routing the two beams in two optical fibers, outside the housing;
  d) collimating two outputs of the two optical fibers prior to transmission through the column of water;
  e) reflecting the two outputs of said step d) back into the housing via a sensor view port,
  f) detecting intensities I1 and I2 of the two outputs reflected in said step e); and
  g) determining the volume attenuation coefficient of the column of water according to:

$$\alpha = \Delta R^{-1} \ln(I_2/I_1)$$

where $\alpha$ = volume attenuation coefficient of the column of water;
  $\Delta R$ = In water path length difference (R1–R2);
  R1 = In-water path length for a first of the two beams of said step b);
  R2 = In-water path length for a second of the two beams of said step b);
  $I_1$ = Intensity at the first of the two beams of said step b);
  $I_2$ = Intensity at the second of the two beams of said step b).

48. The method of claim 47, wherein the light propagated in said step a) is produced by a laser light source.

49. The method of claim 48, wherein the laser light source is one of a solid state laser source and an argon laser source.

50. The method of claim 47, wherein $\Delta R \geq \frac{1}{2}$ meter.

51. The method of claim 47, wherein said step c), the light is split into the two beams such that the two beams have a 1:1 intensity ratio.

52. The method of claim 47, wherein the two optical fibers are attached to an outside of the housing with holding fixtures.

53. The method of claim 47, wherein said method removes an error associated with window fouling of the underwater laser line scanning system.

54. The method of claim 47, wherein the portion of the light is diverted in said step c) with an optical pickoff fiber.

55. The method of claim 47, wherein the portion of the light is reflected in said step d) with a reflecting prism.

56. The method of claim 47, wherein said step g) determines the volume attenuation coefficient simultaneously with detection operations of said underwater laser line scanning system.

57. The method of claim 47, wherein an output of said step b) is utilized to produce a reflectance map of the surface below the column of water.

58. The method of claim 47, wherein the light is propagated in said step a) using a pyramidal scanning mirror and the light is received in said step b) using a pyramidal projecting mirror, operating synchronously with the pyramidal scanning mirror to produce a reflectance map.

59. The method of claim 58, wherein the pyramidal scanning mirror including four sides of 90° wherein a first portion of each of the four sides are used to propagate the light through the column of water and a second portion of each of the four sides provide the portion of the light diverted in said step c).

60. The method of claim 59, wherein the first portion of each of said four sides is 70° and the second portion of each of said four sides is 20°.

61. A transmissometer for measuring a volume attenuation coefficient of a column of water, comprising:

a transmissometer housing;

a light source, producing an optical light beam;

a Y-splitter, splitting the optical light beam into two light beams within said transmissometer housing;

a pressure-proof connector and two optical fibers, routing the two light beams outside said transmissometer housing;

two collimators for collimating outputs of the two optical fibers prior to transmission through the column of water;

a reflecting prism, reflecting the outputs of said two collimators back into said transmissometer housing via a sensor view port wherein a distance between a first of said two collimators and said reflecting prism is R1 and a distance between a second of said two collimators and said reflecting prism is R2;

two detectors for detecting intensities I1 and I2 of the two light beams reflected by said reflecting prism; and a processor for determining the volume attenuation coefficient of the column of water according to:

$$\alpha = \Delta R^{-1} \ln(I_2/I_1)$$

where

α=volume attenuation coefficient of the column of water;
ΔR=In water path length difference (R1–R2);
$I_1$=Intensity at the first of said two detectors; and
$I_2$=Intensity at the second of said two detectors.

62. An underwater laser line scanning system comprising:

a housing;

a light source, producing light;

a scanning mirror, propagating the light through an output window in said housing through a column of water onto a surface below the column of water;

a projection mirror, receiving light reflected by the surface below the column of water via an input window in said housing;

an optical pickoff fiber, diverting a portion of the light propagated by said scanning mirror, a Y-splitter, splitting the portion of the light diverted by said optical pickoff fiber into two light beams within said housing;

a pressure-proof connector and two optical fibers, routing the two light beams outside said housing;

two collimators for collimating outputs of the two optical fibers prior to transmission through the column of water;

a reflecting prism, reflecting the outputs of said two collimators back into said housing via a sensor view port wherein a distance between a first of said two collimators and said reflecting prism is R1 and a distance between a second of said two collimators and said reflecting prism is R2;

a processor for determining the volume attenuation coefficient of the column of water according to:

$$\alpha = \Delta R^{-1} \ln(I_2/I_1)$$

where

α=volume attenuation coefficient of the column of water;
ΔR=In water path length difference (R1–R2);
$I_1$=Intensity at the first of said two detectors; and
$I_2$=Intensity at the second of said two detectors.

* * * * *